(12) United States Patent
Gurge et al.

(10) Patent No.: US 8,784,780 B2
(45) Date of Patent: Jul. 22, 2014

(54) HIGH OIL-CONTENT EMOLLIENT AEROSOL FOAM COMPOSITIONS

(75) Inventors: Ronald M. Gurge, Frankin, MA (US); Mark W. Trumbore, Westford, MA (US); Lisa Chin, Narragansett, RI (US); Poonam S. Hirani, Lexington, MA (US)

(73) Assignee: Precision Dermatology, Inc., Cumberland, RI (US)

( * ) Notice: Subject to any disclaimer, the term of this patent is extended or adjusted under 35 U.S.C. 154(b) by 358 days.

(21) Appl. No.: 13/046,088

(22) Filed: Mar. 11, 2011

(65) Prior Publication Data

US 2011/0305643 A1    Dec. 15, 2011

Related U.S. Application Data

(60) Provisional application No. 61/353,778, filed on Jun. 11, 2010.

(51) Int. Cl.
| | |
|---|---|
| *A61K 9/12* | (2006.01) |
| *A61K 31/00* | (2006.01) |
| *A61P 7/06* | (2006.01) |
| *A61P 7/10* | (2006.01) |
| *A61P 29/00* | (2006.01) |
| *A61P 3/02* | (2006.01) |

(52) U.S. Cl.
USPC ............ 424/45; 424/43; 424/78.05; 514/886; 514/863; 514/859; 514/861; 514/945

(58) Field of Classification Search
USPC ........... 424/45, 43, 78.05; 514/886, 863, 859, 514/861, 945
See application file for complete search history.

(56) References Cited

U.S. PATENT DOCUMENTS

| 5,658,559 A * | 8/1997 | Smith ..................... 424/78.02 |
|---|---|---|
| 2003/0059382 A1 | 3/2003 | Brandt et al. | |
| 2005/0042182 A1 * | 2/2005 | Arkin et al. ..................... 424/47 |
| 2007/0154402 A1 | 7/2007 | Trumbore et al. | |
| 2008/0317679 A1 | 12/2008 | Tamarkin et al. | |
| 2009/0233892 A1 * | 9/2009 | Sen et al. ..................... 514/179 |
| 2009/0257957 A1 * | 10/2009 | Burnier et al. ................. 424/45 |
| 2011/0229417 A1 * | 9/2011 | Gurge et al. .................... 424/45 |

FOREIGN PATENT DOCUMENTS

EP    2108360 A3    10/2009

OTHER PUBLICATIONS

Johnson et al. "Treatment of Seborrheic Dermatitis," Am. Fam. Physician May 1, 2000, 61(9), pp. 2703-2710, accessed at http://www.aafp.org/afp/2000/0501/p2703.html?printable=afp on May 11, 2013 and printed as pp. 1-14.*
Abramovits, W., "A Clinician's Paradigm in the Treatment of Atopic Dermatitis," J. Am Acad Dermatol., 53(1):S70-S77 (2005).
Buys, L.M., "Treatment Options for Atopic Dermatitis," American Family Physician, 75(4):523-528 (2007).
Gottlieb, A.B., "Section A: New and Current Therapies and Vehicles in the Management of Inflammatory Skin Diseases—Therapeutic Options in the Treatment of Psoriasis and Atopic Dermatitis," J Am Acad Dermatol, 53(1):S3-S16 (2005).
Lebwohl, M., "Section B: Optimizing Disease Management—A Clinician's Paradigm in the Treatment of Psoriasis," J Am Acad Dermatol, 53(1):S59-S69 (2005).
van de Kerkhof, PCM et al., "Psoriasis: Consensus on Topical Therapies," J Eur Acad Dermatol Venereol, 22:859-870 (2008).
International Search Report for PCT/US2011/028079 mailed on Nov. 29, 2011.

* cited by examiner

*Primary Examiner* — Mina Haghighatian
(74) *Attorney, Agent, or Firm* — Foley Hoag LLP

(57) ABSTRACT

Described herein are high oil-content emulsions and compositions for the treatment of inflammatory skin disorders. The emulsions may be formulated as aerosol compositions. The aerosol propellant may be a hydrofluoroalkane propellant. The emulsions or compositions may comprise active agents, such as corticosteroids. Also described are methods of treating inflammatory skin disorders, comprising the step of applying to an affected area of a subject in need thereof a therapeutically-effective amount of an inventive emulsion or aerosol composition.

20 Claims, 10 Drawing Sheets

Figure 1

| Component (weight % of the total emulsion) | NB249-90 | NB249-92 | NB249-95 | NB249-96 | NB249-97 | NB249-98 | NB249-99 | NB249-100 | NB296-07 | NB296-14 |
|---|---|---|---|---|---|---|---|---|---|---|
| Hydrocortisone Butyrate | 0.100 | 0.100 | 0.100 | 0.100 | 0.100 | 0.100 | 0.100 | 0.100 | 0.100 | 0.100 |
| Citric Acid | 0.047 | 0.047 | 0.047 | 0.047 | 0.047 | 0.047 | 0.047 | 0.047 | 0.047 | 0.047 |
| Sodium Citrate | 0.027 | 0.027 | 0.027 | 0.027 | 0.027 | 0.027 | 0.027 | 0.027 | 0.027 | 0.027 |
| Ceteth-20 | 0.001 | 0.001 | 0.002 | 0.002 | 0.002 | 0.001 | 0.001 | 0.001 | 0.001 | 0.002 |
| Purified Water | 1.310 | 1.310 | 1.310 | 1.310 | 1.310 | 1.310 | 1.310 | 1.310 | 1.310 | 1.310 |

Figure 2

| Component (weight % of the total emulsion) | NB249-90 | NB249-92 | NB249-95 | NB249-96 | NB249-97 | NB249-98 | NB249-99 | NB249-100 | NB296-07 | NB296-14 |
|---|---|---|---|---|---|---|---|---|---|---|
| Methylparaben | 0.300 | 0.300 | 0.300 | 0.300 | 0.300 | 0.300 | 0.300 | 0.300 | 0.300 | 0.300 |
| Propylparaben | 0.100 | 0.100 | 0.100 | 0.100 | 0.100 | 0.100 | 0.100 | 0.100 | 0.100 | 0.100 |
| Citric Acid | 0.373 | 0.373 | 0.373 | 0.373 | 0.373 | 0.373 | 0.373 | 0.373 | 0.373 | 0.373 |
| Sodium Citrate | 0.293 | 0.293 | 0.293 | 0.293 | 0.293 | 0.293 | 0.293 | 0.293 | 0.293 | 0.293 |
| Glycerin | 10.000 | 10.000 | 10.000 | 10.000 | 5.000 | 5.000 | 5.000 | 5.000 | 5.000 | 5.000 |
| Urea | 0.640 | 0.640 | 0.640 | 0.640 | 0.640 | 0.640 | 0.640 | 0.640 | 0.640 | 0.640 |
| Purified Water | 55.810 | 63.560 | 36.286 | 59.040 | 67.040 | 61.085 | 55.150 | 49.205 | 54.150 | 71.980 |

Figure 3

| Component (weight % of the total emulsion) | NB249-90 | NB249-92 | NB249-95 | NB249-96 | NB249-97 | NB249-98 | NB249-99 | NB249-100 | NB296-07 | NB296-14 |
|---|---|---|---|---|---|---|---|---|---|---|
| Light Mineral Oil | 6.000 | 4.500 | 9.780 | 8.250 | 8.250 | 10.313 | 12.380 | 14.440 | 12.380 | 6.190 |
| White Petrolatum | 12.500 | 9.375 | 22.820 | 5.000 | 5.000 | 6.250 | 7.500 | 8.750 | 7.500 | 3.750 |
| Dimethicone | 1.000 | 0.750 | 1.630 | 1.000 | 1.000 | 1.000 | 1.000 | 1.000 | 1.000 | 1.000 |
| Safflower Oil | | | | 4.500 | 4.500 | 5.625 | 6.750 | 7.880 | 6.750 | 3.375 |
| Butylated Hydroxytoluene | | | | 0.200 | 0.020 | 0.037 | 0.030 | 0.035 | 0.030 | 0.015 |
| Cholesterol | 0.500 | 0.375 | | | | | | | | |
| Ceramides 2 | 0.250 | 0.188 | 0.815 | | | | | | | |
| Ceramides 3 | 0.250 | 0.188 | 0.815 | | | | | | | |
| Ceteth-20 | 1.799 | 1.349 | 2.932 | 2.998 | 1.998 | 2.499 | 2.999 | 3.499 | 2.999 | 1.498 |
| Cetostearyl Alcohol | 7.200 | 5.400 | 11.736 | 6.000 | 4.000 | 5.000 | 6.000 | 7.000 | 6.000 | 3.000 |
| Oleic Acid | 0.750 | 0.563 | | | | | | | 0.500 | 0.500 |
| Stearic Acid | 0.750 | 0.563 | | | | | | | 0.500 | 0.500 |

Figure 4

| Component (% wt/wt) | NB416-01 | NB416-20 | NB416-08 | NB416-02 | NB416-03 | NB416-12 |
|---|---|---|---|---|---|---|
| Betamethasone Dipropionate | 0.05 | 0.05 | | | 0.05 | 0.05 |
| Tretinoin | | | 0.02 | | | 0.02 |
| Calcipotriene | | | | 0.005 | 0.005 | |
| Methylparaben | 0.3 | 0.3 | 0.3 | 0.3 | 0.3 | 0.3 |
| Propylparaben | 0.1 | 0.1 | 0.1 | 0.1 | 0.1 | 0.1 |
| Citric Acid | 0.42 | 0.42 | 0.42 | 0.42 | 0.42 | 0.42 |
| Sodium Citrate | 0.32 | 0.32 | 0.32 | 0.32 | 0.32 | 0.32 |
| Glycerin | 5.00 | 5.00 | 5.00 | 5.00 | 5.00 | 5.00 |
| Urea | 0.64 | 0.64 | 0.64 | 0.64 | 0.64 | 0.64 |
| Purified Water | 56.51 | 56.51 | 56.54 | 56.555 | 56.505 | 56.49 |
| Light Mineral Oil | 12.38 | 2.38 | 12.38 | 12.38 | 12.38 | 12.38 |
| White Petrolatum | 7.50 | 6.85 | 7.50 | 7.50 | 7.50 | 7.50 |
| Dimethicone | 1.00 | 1.00 | 1.00 | 1.00 | 1.00 | 1.00 |
| Safflower Oil | 6.75 | | 6.75 | 6.75 | 6.75 | 6.75 |
| Butylated Hydroxytoluene | 0.03 | 0.03 | 0.03 | 0.03 | 0.03 | 0.03 |
| Ceteth-20 | 3.00 | 3.00 | 3.00 | 3.00 | 3.00 | 3.00 |
| Cetostearyl Alcohol | 6.00 | 6.00 | 6.00 | 6.00 | 6.00 | 6.00 |
| Oleyl Alcohol | | 10.00 | | | | |
| Oleic Acid | | 7.40 | | | | |

| | NB249-87 | NB249-78 | NB296-01 | NB249-94 | NB249-96 | NB249-100 |
|---|---|---|---|---|---|---|
| Hydrocortisone Butyrate | 0.10 | 0.100 | 0.100 | 0.100 | 0.100 | 0.100 |
| Methylparaben | 0.30 | 0.300 | 0.300 | 0.300 | 0.300 | 0.300 |
| Propylparaben | 0.10 | 0.100 | 0.100 | 0.100 | 0.100 | 0.100 |
| Citric Acid | 0.42 | 0.420 | 0.420 | 0.420 | 0.420 | 0.420 |
| Sodium Citrate | 0.32 | 0.320 | 0.320 | 0.320 | 0.320 | 0.320 |
| Glycerin | 10.00 | 10.000 | 5.000 | 10.000 | 10.000 | 5.000 |
| Urea | 0.64 | 0.640 | 0.640 | 0.640 | 0.640 | 0.640 |
| Light Mineral Oil | 4.50 | 6.00 | 6.190 | 9.780 | 8.250 | 14.440 |
| White Petrolatum | 11.25 | 15.00 | 3.750 | 24.450 | 5.000 | 8.750 |
| Dimethicone | 0.75 | 1.00 | 1.000 | 1.630 | 1.000 | 1.000 |
| Safflower Oil | | | 3.375 | | 4.500 | 7.880 |
| Butylated Hydroxytoluene | | | 0.015 | | 0.020 | 0.035 |
| Ceteth-20 | 1.35 | 1.80 | 1.500 | 2.934 | 3.000 | 3.500 |
| Cetostearyl Alcohol | 5.40 | 7.20 | 3.000 | 11.730 | 6.000 | 7.000 |
| Purified Water | 64.87 | 57.12 | 74.290 | 37.596 | 60.350 | 50.515 |

Figure 5

| Lot # | % Liquid Lipids | % Cetostearyl Alcohol | Viscosity (cP) |
|---|---|---|---|
| NB249-87 | 5.25 | 5.4 | 134000 |
| NB249-78 | 7.00 | 7.2 | 204000 |
| NB296-01 | 10.57 | 3.000 | 180000 |
| NB249-94 | 11.41 | 11.73 | 868000 |
| NB249-96 | 13.75 | 6.000 | 368000 |
| NB249-97 | 13.75 | 4.000 | 204000 |
| NB249-98 | 16.94 | 5.000 | 208000 |
| NB249-99 | 20.13 | 6.000 | 259000 |
| NB249-100 | 23.32 | 7.000 | 310000 |

Figure 6

| Product | Form | Density |
|---|---|---|
| NB249-99 | Foam | 0.16 g/cm$^3$ |
| NB249-97 | Foam | 0.15 g/cm$^3$ |
| NB249-98 | Foam | 0.21 g/cm$^3$ |
| NB296-06 | Foam | 0.23 g/cm$^3$ |
| Locoid Cream | Cream | 0.94 g/cm$^3$ |
| Locoid Lipocream | Cream | 0.89 g/cm$^3$ |

Figure 7

| Run | Emollient Oil %wt/wt | Surfactant %wt/wt | Co-Surfactant %wt/wt | Days Stable 134a | Days Stable Blend |
|---|---|---|---|---|---|
| 1 | 23.660 | 6.000 | 7.000 | 84 | 84 |
| 2 | 28.660 | 3.000 | 5.000 | 14 | 14 |
| 3 | 24.910 | 5.250 | 6.500 | 14 | 84 |
| 4 | 26.910 | 3.750 | 6.000 | 7 | 21 |
| 5 | 23.660 | 6.000 | 7.000 | 84 | 84 |
| 6 | 28.660 | 3.000 | 5.000 | 7 | 7 |
| 7 | 25.660 | 4.500 | 6.500 | 7 | 84 |
| 8 | 27.160 | 4.500 | 5.000 | 84 | 14 |
| 9 | 25.660 | 6.000 | 5.000 | 63 | 84 |
| 10 | 25.910 | 5.250 | 5.500 | 84 | 84 |
| 11 | 24.660 | 6.000 | 6.000 | 84 | 84 |
| 12 | 26.660 | 3.000 | 7.000 | 21 | 84 |
| 13 | 26.660 | 3.000 | 7.000 | 28 | 84 |
| 14 | 27.660 | 3.000 | 6.000 | 63 | 14 |

Figure 8

HIGH OIL-CONTENT EMOLLIENT AEROSOL FOAM COMPOSITIONS

RELATED APPLICATIONS

This application claims the benefit of priority to U.S. Provisional Patent Application Ser. No. 61/353,778, filed Jun. 11, 2010.

BACKGROUND

Inflammatory skin disorders are common diseases of the skin that take many forms, including psoriasis, atopic dermatitis, contact dermatitis, xerotic eczema, seborrheic dermatitis, discoid eczema, venous eczema, acne, rosacea, poison ivy, hives, and occupational dermatitis. Inflammatory skin disorders present with several symptoms, including desquamation, erythema, pruritus, and inflammation.

For example, atopic dermatitis (AD) is a disease characterized by dry, cracked, itchy, and inflamed skin, often presenting on greater than 10% of the body surface area. It accounts for 10-20% of all visits to a dermatologist and affects approximately 3% of the US population, most of whom are children. The condition is characterized by intense pruritus (itch) and a course marked by exacerbations and remissions. Higher transepidermal water loss (TEWL) has also been noted in dry skin atopic patients; TEWL is indicative of a disturbed barrier function, and it has been correlated to pruritus intensity in patients. Furthermore, the compromised skin barrier allows excessive water loss through the epidermal layer of the skin and the potential penetration of allergens.

A doctor has three main goals in designing a treatment regime for a patient suffering from an inflammatory skin disorder, such as AD: healing the skin and keeping it healthy; preventing flare ups; and treating symptoms when they do occur. Proper skin care and moisturizing ointments are the mainstays of topical treatment. Moisturizers which improve barrier function have been reported which reduce the prevalence of AD, and can reduce the associated symptoms.

In addition to moisturizers, a variety of medications may be prescribed to help manage the condition. Topical drug treatments for inflammatory skin disorders include steroids, calcineurin inhibitors, retinoids, vitamin D analogues, tars, anthralin, and keratolytics. However, the number of active ingredients is limited, and the range of dosage forms for these active agents is narrow.

There exists a need for stable, non-irritating topical formulations for the treatment of inflammatory skin disorders.

SUMMARY OF THE INVENTION

In certain embodiments, the invention relates to an emulsion, comprising: an oil phase, wherein the oil phase comprises an emulsifier or surfactant, a first moisturizer or first emollient, and a first antioxidant or first preservative; an aqueous phase, wherein the aqueous phase comprises water, a second moisturizer or second emollient, and a second antioxidant or second preservative; and an active agent.

In certain embodiments, the invention relates to a composition, wherein the composition comprises an emulsion, a propellant, and a purge gas; and the emulsion comprises an oil phase, wherein the oil phase comprises an emulsifier or surfactant, a first moisturizer or first emollient, and a first antioxidant or first preservative; an aqueous phase, wherein the aqueous phase comprises water, a second moisturizer or second emollient, and a second antioxidant or second preservative; and an active agent In certain embodiments, the invention relates to a method of treating an inflammatory skin disorder, comprising the step of applying to an affected area of a subject in need thereof a therapeutically-effective amount of any one of the aforementioned emulsions or compositions.

BRIEF DESCRIPTION OF THE FIGURES

FIG. 1 tabulates the constituents of the drug phase (and their relative quantities in the total emulsion) of various embodiments of emulsions of the invention. The drug phase is combined with an aqueous phase and an oil phase to form an emulsion of the invention.

FIG. 2 tabulates the constituents of the aqueous phase (and their relative quantities in the total emulsion) of various embodiments of emulsions of the invention. The aqueous phase is combined with a drug phase and an oil phase to form an emulsion of the invention.

FIG. 3 tabulates the constituents of the oil phase (and their relative quantities in the total emulsion) of various embodiments of emulsions of the invention. The oil phase is combined with a drug phase and an aqueous phase to form an emulsion of the invention.

FIG. 4 tabulates the constituents (and their relative quantities) of various embodiments of emulsions of the invention.

FIG. 5 tabulates the constituents (and their relative quantities) of various embodiments of emulsions of the invention.

FIG. 6 tabulates the viscosity of various emulsions of the invention as a function of changes in emulsion composition.

FIG. 7 tabulates a comparison of the densities of various compositions of the invention and commercially-available creams.

FIG. 8 tabulates the physical stability at 40° C. of various compositions of the invention as a function of changes in emulsion composition.

DETAILED DESCRIPTION OF THE INVENTION

Overview

Figure 9:
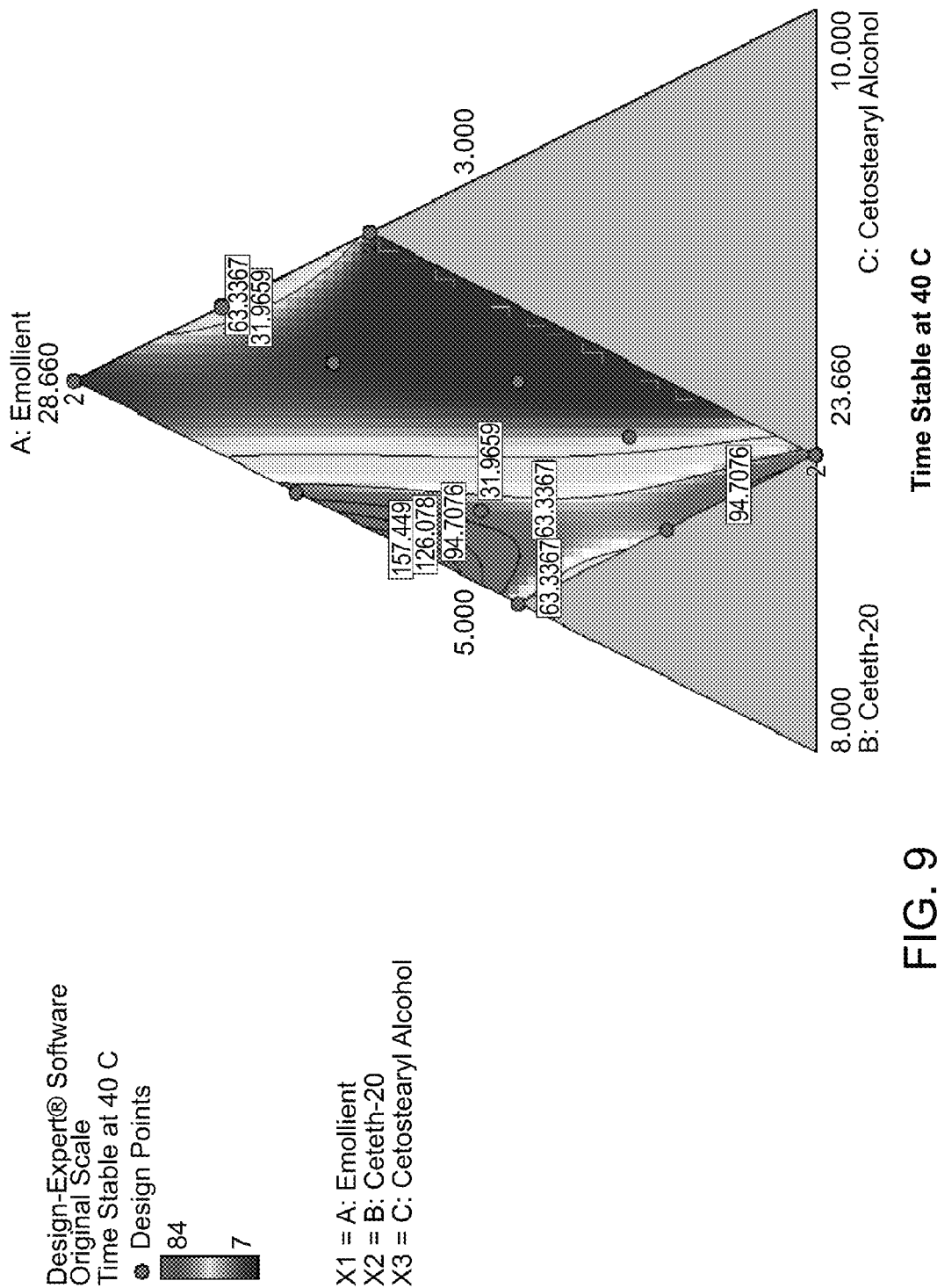
FIG. 9 is a schematic representation of the dependence of composition physical stability (days stable, ranging from 7 (black) to 84 (gray), with light gray in between) on the ratios of emollient oil, Ceteth-20, and cetostearyl alcohol in the presence of 1,1,1,2-tetrafluoroethane. It is interesting to note that the stability of these formulations is relatively insensitive to the concentration of emollient in the formulation (vertical axis).

In certain embodiments, the invention relates to oil-in-water emulsions. In certain embodiments, the compositions do not contain volatile lower alcohols (e.g., ethanol). In certain embodiments, the compositions comprise an aerosol propellant. In certain embodiments, the aerosol propellant is a hydrofluoroalkane (HFA) propellant. In certain embodiments, the identity of the HFA propellant affects the stability of the compositions.

In certain embodiments, the invention relates to high-viscosity emulsions. In certain embodiments, the emulsions contain greater than about 15% oil phase components by weight of the emulsion. In certain embodiments, the emulsions contain less than about 80% aqueous phase components.

In certain embodiments, the compositions produce a foam upon actuation of an aerosol container charged with the composition. In certain embodiments, the compositions immediately produce a foam upon actuation of an aerosol container charged with the composition. In certain embodiments, the foams are stable against collapse. In certain embodiments, the foams are both time- and temperature-stable. In certain embodiments, the foam is moisturizing. In certain embodiments, the foam is non-irritating. In certain embodiments, the dispensed foam has a density between about 0.05 and about 0.5 g/cm$^3$. In certain embodiments, the foam rubs-in quickly without a greasy residue. In certain embodiments, the dispensed foam is easily spread over large body surface areas. In certain embodiments, the foam rapidly collapses when subjected to shear forces, allowing for quick and efficient application to large body surface areas. In certain embodiments, the dispensed foam is compatible with a wide range of active pharmaceutical ingredients. In certain embodiments, the dispensed foam is suitable for the topical treatment of inflammatory skin disorders.

In certain embodiments, the dispensed foam is as effective for the treatment of inflammatory skin disorders as currently commercially-available prescription creams, lotions, and ointments.

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, a "cream" is an opaque, viscous, non-greasy to mildly-greasy emulsion or suspension semisolid intended for external application to the skin that tends to mostly evaporate or be absorbed when rubbed into the skin. The material contains <50% of hydrocarbons or polyethylene glycols as the vehicle and/or >20% volatiles (as measured by loss on drying to a constant weight at about 105° C.).

As used herein, a "lotion" is an opaque, thin, non-greasy emulsion-based liquid intended for external application to the skin that tends to evaporate rapidly with a cooling sensation when rubbed into the skin. The material generally contains a water based composition with >50% volatiles (as measured by loss on drying to a constant weight at about 105° C.).

Exemplary Constituents of Emulsions and Compositions of the Invention

Exemplary identities of various constituents of the compositions of the present invention are described below.

1. Propellants

There are several possible choices of propellants for an aerosol foam, including, but not limited to, CFCs, hydrocarbons, compressed gases, and HFAs. The Montreal Protocol has banned the use of CFCs (chlorofluorocarbons) due to their ability to deplete the ozone layer. Montreal Protocol on Substances that Deplete the Ozone Layer, United Nations Environmental Programme, 1987. In contrast, hydrocarbon propellants demonstrate very low reactivity and good resistance to free-radical attack. However, hydrocarbon propellants are highly flammable. Moreover, compressed inert gases, such as nitrogen and carbon dioxide, can be used as an aerosol propellant. While offering good chemical stability due to their inertness, they are unable to provide consistent product delivery throughout the life of an aerosol can due to their high vapor pressures. Fortunately, HFAs (hydrofluoroalkanes, also known as hydrofluorocarbons, or HFCs) are pharmaceutically acceptable, generally non-reactive, and ozone-friendly.

In one embodiment, the propellant is a HFA or a mixture of one or more hydrofluoroalkanes. Suitable hydrofluoroalkanes include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. Hydrocarbon as well as chlorofluorocarbon (CFC) propellants can also be used in the present invention.

2. Vehicles

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers and surfactants) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, and methylbenzethonium chloride. Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, behentrimonium methosulfate-cetearyl alcohol, non-ionic emulsifiers like emulsifying wax, polyoxyethylene oleyl ether, PEG-40 stearate, cetostearyl alcohol (cetearyl alcohol), ceteareth-12, ceteareth-20, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-100 stearate, glyceryl stearate and PEG-100 stearate, ceramide 2, ceramide 3, stearic acid, cholesterol, steareth-2, and steareth-20, or combinations/mixtures thereof, as well as cationic emulsifiers like stearamidopropyl dimethylamine and behentrimonium methosul fate, or combinations/mixtures thereof.

4. Moisturizers, Emollients, and Humectants

One of the most important aspects of topical products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, butylene glycol, sodium PCA, sodium hyaluronate, and polyethylene glycol (PEG), such as CARBOWAX PEG 200, CARBOWAX PEG 400, and CARBOWAX PEG 800.

Suitable emollients or humectants for use in the formulations of the present invention include, but are not limited to, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, and dicaprylate/dicaprate.

In addition, appropriate combinations and mixtures of any of these moisturizing agents and emollients may be used in accordance with the present invention.

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; sorbic acid; benzoic acid; formaldehyde; citric acid; sodium citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, sodium ascorbate/ascorbic acid, ascorbyl palmitate, propyl gallate, and chelating agents like EDTA (e.g., disodium EDTA), citric acid, and sodium citrate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

6.1 Antibiotics

Representative antibiotics include, without limitation, benzoyl peroxide, octopirox, erythromycin, zinc, tetracyclin, triclosan, azelaic acid and its derivatives, phenoxy ethanol and phenoxy propanol, ethyl acetate, clindamycin (e.g., clindamycin phosphate) and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

6.2 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamiate, a flufenamic acid derivative, is particularly useful for topical application.

6.3 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters (including betamethasone dipropionate), chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

6.4 Anesthetics

Suitable anesthetics include the aminoacylanilide compounds such as lidocaine, prilocaine, bupivacaine, levo-bupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

6.5 Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, clindamycin phosphate, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

6.6 Keratolytic Agents

Suitable keratolytic agents include, but are not limited to, urea, salicylic acid, papain, sulfur, glycolic acid, pyruvic acid, resorcinol, N-acetylcysteine, retinoids such as retinoic acid (e.g., tretinoin) and its derivatives (e.g., cis and trans, esters), alpha hydroxy acids, beta hydroxy acids, coal tar, and combinations thereof.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents) for use in the formulations of the present invention include, but are not limited to, protective colloids or non-ionic gums such as hydroxyethylcellulose, xanthan gum, and sclerotium gum, as well as magnesium aluminum silicate, silica, microcrystalline wax, beeswax, paraffin, and cetyl palmitate. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate).

For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of skin soothing agents include, but are not limited to, allantoin, aloe, avocado oil, green tea extract, hops extract, chamomile extract, colloidal oatmeal, calamine, cucumber extract, and combinations thereof Examples of vitamins include, but are not limited to, vitamins A, D, E, K, and combinations thereof Vitamin analogues are also contemplated; for example the vitamin D analogues calcipotriene or calcipotriol.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof Suitable fragrances and colors may be used in the formulations of the present invention. Examples of fragrances and colors suitable for use in topical products are known in the art.

Suitable immunomodulators include, but are not limited to, tetrachlorodecaoxide, deoxycholic acid, tacrolimus, pimecrolimus, and beta-glucan.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

Exemplary Emulsions of the Invention

In certain embodiments, the invention relates to an emulsion, comprising:
  an oil phase, wherein the oil phase comprises an emulsifier or surfactant, a first moisturizer or first emollient, and a first antioxidant or first preservative;
  an aqueous phase, wherein the aqueous phase comprises water, a second moisturizer or second emollient, and a second antioxidant or second preservative; and
  an active agent.

In certain embodiments, the invention relates to an emulsion, consisting essentially of:
  an oil phase, wherein the oil phase consists essentially of an emulsifier or surfactant, a first moisturizer or first emollient, and a first antioxidant or first preservative;
  an aqueous phase, wherein the aqueous phase consists essentially of water, a second moisturizer or second emollient, and a second antioxidant or second preservative; and
  an active agent.

In certain embodiments, the invention relates to an emulsion, consisting of:
- an oil phase, wherein the oil phase consists of an emulsifier or surfactant, a first moisturizer or first emollient, and a first antioxidant or first preservative;
- an aqueous phase, wherein the aqueous phase consists of water, a second moisturizer or second emollient, and a second antioxidant or second preservative; and
- an active agent.

In certain embodiments, the invention relates to an emulsion, comprising:
- Ceteth-20, from about 1% to about 5% by weight of the emulsion;
- cetostearyl alcohol, from about 3% to about 9% by weight of the emulsion;
- mineral oil, from about 1% to about 18% by weight of the emulsion;
- petrolatum, from about 3% to about 11% by weight of the emulsion;
- dimethicone, from about 0.5% to about 2.0% by weight of the emulsion;
- safflower oil, from about 0% to about 11% by weight of the emulsion;
- oleic acid, from about 0% to about 11% by weight of the emulsion;
- stearic acid, from about 0% to about 1% by weight of the emulsion;
- oleyl alcohol, from about 0% to about 15% by weight of the emulsion;
- butylated hydroxytoluene, from about 0.01% to about 0.05% by weight of the emulsion;
- water, from about 27% to about 82% by weight of the emulsion;
- glycerin, from about 2.5% to about 7.5% by weight of the emulsion;
- urea, from about 0.3% to about 0.9% by weight of the emulsion;
- citric acid, from about 0.2% to about 0.6% by weight of the emulsion;
- sodium citrate, from about 0.1% to about 0.5% by weight of the emulsion;
- methylparaben, from about 0.1% to about 0.5% by weight of the emulsion;
- propylparaben, from about 0.05% to about 0.20% by weight of the emulsion; and
- hydrocortisone butyrate, from about 0.05% to about 0.15% by weight of the emulsion.

In certain embodiments, the invention relates to an emulsion, consisting essentially of:
- Ceteth-20, from about 1% to about 5% by weight of the emulsion;
- cetostearyl alcohol, from about 3% to about 9% by weight of the emulsion;
- mineral oil, from about 1% to about 18% by weight of the emulsion;
- petrolatum, from about 3% to about 11% by weight of the emulsion;
- dimethicone, from about 0.5% to about 2.0% by weight of the emulsion;
- safflower oil, from about 0% to about 11% by weight of the emulsion;
- oleic acid, from about 0% to about 11% by weight of the emulsion;
- stearic acid, from about 0% to about 1% by weight of the emulsion;
- oleyl alcohol, from about 0% to about 15% by weight of the emulsion;
- butylated hydroxytoluene, from about 0.01% to about 0.05% by weight of the emulsion;
- water, from about 27% to about 82% by weight of the emulsion;
- glycerin, from about 2.5% to about 7.5% by weight of the emulsion;
- urea, from about 0.3% to about 0.9% by weight of the emulsion;
- citric acid, from about 0.2% to about 0.6% by weight of the emulsion;
- sodium citrate, from about 0.1% to about 0.5% by weight of the emulsion;
- methylparaben, from about 0.1% to about 0.5% by weight of the emulsion;
- propylparaben, from about 0.05% to about 0.20% by weight of the emulsion; and
- hydrocortisone butyrate, from about 0.05% to about 0.15% by weight of the emulsion.

In certain embodiments, the invention relates to an emulsion, consisting of:
- Ceteth-20, from about 1% to about 5% by weight of the emulsion;
- cetostearyl alcohol, from about 3% to about 9% by weight of the emulsion;
- mineral oil, from about 1% to about 18% by weight of the emulsion;
- petrolatum, from about 3% to about 11% by weight of the emulsion;
- dimethicone, from about 0.5% to about 2.0% by weight of the emulsion;
- safflower oil, from about 0% to about 11% by weight of the emulsion;
- oleic acid, from about 0% to about 11% by weight of the emulsion;
- stearic acid, from about 0% to about 1% by weight of the emulsion;
- oleyl alcohol, from about 0% to about 15% by weight of the emulsion;
- butylated hydroxytoluene, from about 0.01% to about 0.05% by weight of the emulsion;
- water, from about 27% to about 82% by weight of the emulsion;
- glycerin, from about 2.5% to about 7.5% by weight of the emulsion;
- urea, from about 0.3% to about 0.9% by weight of the emulsion;
- citric acid, from about 0.2% to about 0.6% by weight of the emulsion;
- sodium citrate, from about 0.1% to about 0.5% by weight of the emulsion;
- methylparaben, from about 0.1% to about 0.5% by weight of the emulsion;
- propylparaben, from about 0.05% to about 0.20% by weight of the emulsion; and
- hydrocortisone butyrate, from about 0.05% to about 0.15% by weight of the emulsion.

In certain embodiments, the invention relates to an emulsion, comprising:
- Ceteth-20, in about 3.00% by weight of the emulsion;
- cetostearyl alcohol, in about 6.00% by weight of the emulsion;
- mineral oil, in about 12.38% by weight of the emulsion;
- petrolatum, in about 7.50% by weight of the emulsion;
- dimethicone, in about 1.00% by weight of the emulsion;
- safflower oil, in about 6.75% by weight of the emulsion;
- butylated hydroxytoluene, in about 0.03% by weight of the emulsion;

water, in about 54.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 54.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 54.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
oleic acid, in about 0.50% by weight of the emulsion;
stearic acid, in about 0.50% by weight of the emulsion;
butylated hydroxytoluene, in about 0.03% by weight of the emulsion;
water, in about 55.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
oleic acid, in about 0.50% by weight of the emulsion;
stearic acid, in about 0.50% by weight of the emulsion;
butylated hydroxytoluene, in about 0.03% by weight of the emulsion;
water, in about 55.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
oleic acid, in about 0.50% by weight of the emulsion;
stearic acid, in about 0.50% by weight of the emulsion;
butylated hydroxytoluene, in about 0.03% by weight of the emulsion;
water, in about 55.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion.

In certain embodiments, the invention relates to an emulsion, comprising:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;

safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
betamethasone dipropionate, from about 0.02% to about 0.08% by weight of the emulsion.

In certain embodiments, the invention relates to an emulsion, consisting essentially of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
betamethasone dipropionate, from about 0.02% to about 0.08% by weight of the emulsion.

In certain embodiments, the invention relates to an emulsion, consisting of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
betamethasone dipropionate, from about 0.02% to about 0.08% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;

safflower oil, in about 6.75% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 2.38% by weight of the emulsion;
petrolatum, in about 6.85% by weight of the emulsion;
dimethicone, in about 1.00% by weight of the emulsion;
oleic acid, in about 7.40% by weight of the emulsion;
oleyl alcohol, in about 10.00% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 2.38% by weight of the emulsion;
petrolatum, in about 6.85% by weight of the emulsion;
dimethicone, in about 1.00% by weight of the emulsion;
oleic acid, in about 7.40% by weight of the emulsion;
oleyl alcohol, in about 10.00% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 2.38% by weight of the emulsion;
petrolatum, in about 6.85% by weight of the emulsion;
dimethicone, in about 1.00% by weight of the emulsion;
oleic acid, in about 7.40% by weight of the emulsion;
oleyl alcohol, in about 10.00% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion.

In certain embodiments, the invention relates to an emulsion, comprising:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;

methylparaben, from about 0.1% to about 0.5% by weight of the emulsion;
propylparaben, from about 0.05% to about 0.20% by weight of the emulsion; and
tretinoin, from about 0.01% to about 0.03% by weight of the emulsion.

In certain embodiments, the invention relates to an emulsion, consisting essentially of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
tretinoin, from about 0.01% to about 0.03% by weight of the emulsion.

In certain embodiments, the invention relates to an emulsion, consisting of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
tretinoin, from about 0.01% to about 0.03% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.54% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
tretinoin, in about 0.02% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.54% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
tretinoin, in about 0.02% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;

water, in about 56.54% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
tretinoin, in about 0.02% by weight of the emulsion.

In certain embodiments, the invention relates to an emulsion, comprising:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
calcipotriene, from about 0.002% to about 0.008% by weight of the emulsion.

In certain embodiments, the invention relates to an emulsion, consisting essentially of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
calcipotriene, from about 0.002% to about 0.008% by weight of the emulsion.

In certain embodiments, the invention relates to an emulsion, consisting of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion; and
calcipotriene, from about 0.002% to about 0.008% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;

water, in about 56.555% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
calcipotriene, in about 0.005% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.555% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
calcipotriene, in about 0.005% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.555% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
calcipotriene, in about 0.005% by weight of the emulsion.

In certain embodiments, the invention relates to an emulsion, comprising:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion;
betamethasone dipropionate, from about 0.02% to about 0.08% by weight of the emulsion; and
calcipotriene, from about 0.002% to about 0.008% by weight of the emulsion.

In certain embodiments, the invention relates to an emulsion, consisting essentially of:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion;
betamethasone dipropionate, from about 0.02% to about 0.08% by weight of the emulsion; and
calcipotriene, from about 0.002% to about 0.008% by weight of the emulsion.

In certain embodiments, the invention relates to an emulsion, consisting of:
Ceteth-20, from about 1% to about 5% by weight of the emulsion;

cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;
propylparaben, from about 0.05% to about 0.20% by weight of the emulsion;
betamethasone dipropionate, from about 0.02% to about 0.08% by weight of the emulsion; and
calcipotriene, from about 0.002% to about 0.008% by weight of the emulsion.

In certain embodiments, the invention relates to an emulsion, comprising:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.505% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion;
betamethasone dipropionate, in about 0.05% by weight of the emulsion; and
calcipotriene, in about 0.005% by weight of the emulsion.

In certain embodiments, the invention relates to an emulsion, consisting essentially of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.505% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion;
betamethasone dipropionate, in about 0.05% by weight of the emulsion; and
calcipotriene, in about 0.005% by weight of the emulsion.

In certain embodiments, the invention relates to an emulsion, consisting of:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
safflower oil, in about 6.75% by weight of the emulsion;
butylated hydroxytoluene, in about 0.03% by weight of the emulsion;
water, in about 56.505% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion;
betamethasone dipropionate, in about 0.05% by weight of the emulsion; and
calcipotriene, in about 0.005% by weight of the emulsion.

In certain embodiments, the invention relates to an emulsion, comprising:
Ceteth-20, from about 1% to about 5% by weight of the emulsion;
cetostearyl alcohol, from about 3% to about 9% by weight of the emulsion;
mineral oil, from about 1% to about 18% by weight of the emulsion;
petrolatum, from about 3% to about 11% by weight of the emulsion;
dimethicone, from about 0.5% to about 2.0% by weight of the emulsion;
safflower oil, from about 0% to about 11% by weight of the emulsion;
oleic acid, from about 0% to about 11% by weight of the emulsion;
stearic acid, from about 0% to about 1% by weight of the emulsion;
oleyl alcohol, from about 0% to about 15% by weight of the emulsion;
butylated hydroxytoluene, from about 0.01% to about 0.05% by weight of the emulsion;
water, from about 27% to about 82% by weight of the emulsion;
glycerin, from about 2.5% to about 7.5% by weight of the emulsion;
urea, from about 0.3% to about 0.9% by weight of the emulsion;
citric acid, from about 0.2% to about 0.6% by weight of the emulsion;
sodium citrate, from about 0.1% to about 0.5% by weight of the emulsion;
methylparaben, from about 0.1% to about 0.5% by weight of the emulsion;

propylparaben, from about 0.05% to about 0.20% by weight of the emulsion;

betamethasone dipropionate, from about 0.02% to about 0.08% by weight of the emulsion; and tretinoin, from about 0.02% to about 0.03% by weight of the emulsion.

In certain embodiments, the invention relates to an emulsion, consisting essentially of:

Ceteth-20, from about 1% to about 5% by weight of the emulsion;

cetostearyl alcohol, from about 3% to about 9% by weight of the emulsion;

mineral oil, from about 1% to about 18% by weight of the emulsion;

petrolatum, from about 3% to about 11% by weight of the emulsion;

dimethicone, from about 0.5% to about 2.0% by weight of the emulsion;

safflower oil, from about 0% to about 11% by weight of the emulsion;

oleic acid, from about 0% to about 11% by weight of the emulsion;

stearic acid, from about 0% to about 1% by weight of the emulsion;

oleyl alcohol, from about 0% to about 15% by weight of the emulsion;

butylated hydroxytoluene, from about 0.01% to about 0.05% by weight of the emulsion;

water, from about 27% to about 82% by weight of the emulsion;

glycerin, from about 2.5% to about 7.5% by weight of the emulsion;

urea, from about 0.3% to about 0.9% by weight of the emulsion;

citric acid, from about 0.2% to about 0.6% by weight of the emulsion;

sodium citrate, from about 0.1% to about 0.5% by weight of the emulsion;

methylparaben, from about 0.1% to about 0.5% by weight of the emulsion;

propylparaben, from about 0.05% to about 0.20% by weight of the emulsion;

betamethasone dipropionate, from about 0.02% to about 0.08% by weight of the emulsion; and tretinoin, from about 0.02% to about 0.03% by weight of the emulsion.

In certain embodiments, the invention relates to an emulsion, consisting of:

Ceteth-20, from about 1% to about 5% by weight of the emulsion;

cetostearyl alcohol, from about 3% to about 9% by weight of the emulsion;

mineral oil, from about 1% to about 18% by weight of the emulsion;

petrolatum, from about 3% to about 11% by weight of the emulsion;

dimethicone, from about 0.5% to about 2.0% by weight of the emulsion;

safflower oil, from about 0% to about 11% by weight of the emulsion;

oleic acid, from about 0% to about 11% by weight of the emulsion;

stearic acid, from about 0% to about 1% by weight of the emulsion;

oleyl alcohol, from about 0% to about 15% by weight of the emulsion;

butylated hydroxytoluene, from about 0.01% to about 0.05% by weight of the emulsion;

water, from about 27% to about 82% by weight of the emulsion;

glycerin, from about 2.5% to about 7.5% by weight of the emulsion;

urea, from about 0.3% to about 0.9% by weight of the emulsion;

citric acid, from about 0.2% to about 0.6% by weight of the emulsion;

sodium citrate, from about 0.1% to about 0.5% by weight of the emulsion;

methylparaben, from about 0.1% to about 0.5% by weight of the emulsion;

propylparaben, from about 0.05% to about 0.20% by weight of the emulsion;

betamethasone dipropionate, from about 0.02% to about 0.08% by weight of the emulsion; and tretinoin, from about 0.02% to about 0.03% by weight of the emulsion.

In certain embodiments, the invention relates to an emulsion, comprising:

Ceteth-20, in about 3.00% by weight of the emulsion;

cetostearyl alcohol, in about 6.00% by weight of the emulsion;

mineral oil, in about 12.38% by weight of the emulsion;

petrolatum, in about 7.50% by weight of the emulsion;

dimethicone, in about 1.00% by weight of the emulsion;

safflower oil, in about 6.75% by weight of the emulsion;

butylated hydroxytoluene, in about 0.03% by weight of the emulsion;

water, in about 56.49% by weight of the emulsion;

glycerin, in about 5.00% by weight of the emulsion;

urea, in about 0.64% by weight of the emulsion;

citric acid, in about 0.42% by weight of the emulsion;

sodium citrate, in about 0.32% by weight of the emulsion;

methylparaben, in about 0.30% by weight of the emulsion;

propylparaben, in about 0.10% by weight of the emulsion;

betamethasone dipropionate, in about 0.05% by weight of the emulsion; and tretinoin, in about 0.02% by weight of the emulsion.

Exemplary Components of the Oil Phase

As outlined above, in certain embodiments, the invention relates to an emulsion comprising an oil phase, wherein the oil phase comprises an emulsifier or surfactant, a first moisturizer or first emollient, and a first antioxidant or first preservative. The components described below may be present in the oil phase of any one of the aforementioned emulsions.

In certain embodiments, the invention relates to any one of the aforementioned emulsions, wherein the emulsifier or surfactant is selected from the group consisting of: polysorbate 20, polysorbate 40, polysorbate 60, polysorbate 80, steareth-10, sodium dodecyl sulfate, lauryl dimethyl amine oxide, cetyltrimethylammonium bromide, polyethoxylated alcohols, polyoxyethylene sorbitan, octoxynol, N,N-dimethyldodecylamine-N-oxide, hexadecyltrimethylammonium bromide, polyoxyl 10 lauryl ether, sodium deoxycholate, sodium cholate, polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate, ceteareth-10 phosphate, methylbenzethonium chloride, behentrimonium methosulfate-cetearyl alcohol, non-ionic emulsifiers like emulsifying wax, polyoxyethylene oleyl ether, PEG-40 stearate, cetostearyl alcohol, ceteareth-12, ceteareth-20, ceteareth-30, ceteareth alcohol, Ceteth-20, oleic acid, oleyl alcohol, glyceryl stearate, PEG-100 stearate, glyceryl stearate and PEG-100 stearate, steareth-2, steareth-20, stearic acid, cholesterol, ceramide 2, ceramide 3, stearamidopropyl dimethylamine, behentrimonium methosulfate, and combinations/mixtures thereof.

In certain embodiments, the invention relates to any one of the aforementioned emulsions, wherein the emulsifier or surfactant is selected from the group consisting of Ceteth-20, cetostearyl alcohol, and combinations/mixtures thereof.

In certain embodiments, the invention relates to any one of the aforementioned emulsions, wherein the emulsifier or surfactant is present in an amount from about 4% to about 20% by weight of the emulsion. In certain embodiments, the emulsifier or surfactant is present in an amount from about 6% to about 12% by weight of the emulsion. In certain embodiments, the emulsifier or surfactant is present in an amount of about 6%, about 7%, about 8%, about 9%, about 10%, about 11%, or about 12% by weight of the emulsion.

In certain embodiments, the invention relates to any one of the aforementioned emulsions, wherein the emulsifier or surfactant comprises Ceteth-20. In certain embodiments, the Ceteth-20 is present in an amount from about 1% to about 5% by weight of the emulsion. In certain embodiments, the Ceteth-20 is present in an amount from about 2% to about 4% by weight of the emulsion. In certain embodiments, the Ceteth-20 is present in about 2.0%, about 2.5%, about 3.0%, about 3.5%, or about 4.0% by weight of the emulsion.

In certain embodiments, the invention relates to any one of the aforementioned emulsions, wherein the emulsifier or surfactant comprises cetostearyl alcohol (cetearyl alcohol). In certain embodiments, the cetostearyl alcohol is present in an amount from about 3% to about 9% by weight of the emulsion. In certain embodiments, the cetostearyl alcohol is present in an amount from about 4% to about 8% by weight of the emulsion. In certain embodiments, the cetostearyl alcohol is present in an amount from about 5.4% to about 6% by weight of the emulsion. In certain embodiments, the cetostearyl alcohol is present in an amount from about 5% to about 7% by weight of the emulsion. In certain embodiments, the cetostearyl alcohol is present in about 4%, about 5%, about 6%, about 7%, or about 8% by weight of the emulsion.

In certain embodiments, the invention relates to any one of the aforementioned emulsions, wherein the first moisturizer or first emollient is selected from the group consisting of petrolatum, lactic acid, glycerol, propylene glycol, butylene glycol, sodium PCA, sodium hyaluronate, CARBOWAX PEG 200, CARBOWAX PEG 400, CARBOWAX PEG 800, cetyl palmitate, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, propylene glycol, *Theobroma grandiflorum* seed butter, ceramide 2, hydroxypropyl bispalmitamide MEA, hydroxypropyl bislauramide MEA, hydroxypropyl bisisostearamide MEA, 1,3-bis(N-2-(hydroxyethyl) stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, dicaprylate/dicaprate, and combinations/mixtures thereof.

In certain embodiments, the invention relates to any one of the aforementioned emulsions, wherein the first moisturizer or first emollient is selected from the group consisting of mineral oil, petrolatum, dimethicone, safflower oil, oleic acid, stearic acid, oleyl alcohol, and combinations/mixtures thereof.

In certain embodiments, the invention relates to any one of the aforementioned emulsions, wherein the first moisturizer or first emollient is present in an amount from about 14% to about 42% by weight of the emulsion. In certain embodiments, the first moisturizer or first emollient is present in an amount from about 18% to about 38% by weight of the emulsion. In certain embodiments, the first moisturizer or first emollient is present in an amount of about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, or about 38% by weight of the emulsion.

In certain embodiments, the invention relates to any one of the aforementioned emulsions, wherein the first moisturizer or first emollient comprises mineral oil. In certain embodiments, the mineral oil is present in an amount from about 1% to about 18% by weight of the emulsion. In certain embodiments, the mineral oil is present in an amount from about 2% to about 16% by weight of the emulsion. In certain embodiments, the mineral oil is present in about 2%, about 4%, about 6%, about 8%, about 10%, about 12%, about 14%, or about 16% by weight of the emulsion. In certain embodiments, the mineral oil is light mineral oil.

In certain embodiments, the invention relates to any one of the aforementioned emulsions, wherein the first moisturizer or first emollient comprises petrolatum. In certain embodiments, the petrolatum is present in an amount from about 3% to about 11% by weight of the emulsion. In certain embodiments, the petrolatum is present in an amount from about 4% to about 10% by weight of the emulsion. In certain embodiments, the petrolatum is present in about 4%, about 5%, about 6%, about 7%, about 8%, about 9%, or about 10% by weight of the emulsion. In certain embodiments, the petrolatum is white petrolatum.

In certain embodiments, the invention relates to any one of the aforementioned emulsions, wherein the first moisturizer or first emollient comprises dimethicone. In certain embodiments, the dimethicone is present in an amount from about 0.5% to about 2% by weight of the emulsion. In certain embodiments, the dimethicone is present in an amount from about 0.5% to about 1.5% by weight of the emulsion. In certain embodiments, the dimethicone is present in about 0.5%, about 0.6%, about 0.7%, about 0.8%, about 0.9%, about 1.0%, about 1.1%, about 1.2%, about 1.3%, about 1.4%, or about 1.5% by weight of the emulsion.

In certain embodiments, the invention relates to any one of the aforementioned emulsions, wherein the first moisturizer or first emollient comprises safflower oil. In certain embodiments, the safflower oil is present in an amount from about 0% to about 11% by weight of the emulsion. In certain embodiments, the safflower oil is present in an amount from about 0% to about 10% by weight of the emulsion. In certain embodiments, the safflower oil is present in about 0%, about 1%, about 2%, about 3%, about 4%, about 5%, about 6%, about 7%, about 8%, about 9%, or about 10% by weight of the emulsion.

In certain embodiments, the invention relates to any one of the aforementioned emulsions, wherein the first moisturizer or first emollient comprises oleic acid. In certain embodiments, the oleic acid is present in an amount from about 0% to about 11% by weight of the emulsion. In certain embodiments, the oleic acid is present in an amount from about 0% to about 10% by weight of the emulsion. In certain embodiments, the oleic acid is present in about 0%, about 1%, about 2%, about 3%, about 4%, about 5%, about 6%, about 7%, about 8%, about 9%, or about 10% by weight of the emulsion.

In certain embodiments, the invention relates to any one of the aforementioned emulsions, wherein the first moisturizer or first emollient comprises stearic acid. In certain embodiments, the stearic acid is present in an amount from about 0% to about 1.0% by weight of the emulsion. In certain embodiments, the stearic acid is present in an amount from about 0% to about 0.8% by weight of the emulsion. In certain embodiments, the stearic acid is present in about 0%, about 0.1%, about 0.2%, about 0.3%, about 0.4%, about 0.5%, about 0.6%, about 0.7%, or about 0.8% by weight of the emulsion.

In certain embodiments, the invention relates to any one of the aforementioned emulsions, wherein the first moisturizer or first emollient comprises oleyl alcohol. In certain embodiments, the oleyl alcohol is present in an amount from about 0% to about 15% by weight of the emulsion. In certain embodiments, the oleyl alcohol is present in an amount from about 0% to about 13% by weight of the emulsion. In certain embodiments, the oleyl alcohol is present in about 0%, about 1%, about 2%, about 3%, about 4%, about 5%, about 6%, about 7%, about 8%, about 9%, about 10%, about 11%, about 12%, or about 13% by weight of the emulsion.

In certain embodiments, the invention relates to any one of the aforementioned emulsions, wherein the oil phase of the emulsion comprises liquid lipids. In certain embodiments, the liquid lipids are first moisturizers or first emollients. In certain embodiments, the liquid lipids are present in an amount from about 15% to about 25% by weight of the emulsion. In certain embodiments, the liquid lipids are present in an amount from about 18% to about 22% by weight of the emulsion. In certain embodiments, the liquid lipids are selected from the group consisting of mineral oil, dimethicone, safflower oil, oleic acid, oleyl alcohol, and combinations/mixtures thereof.

In certain embodiments, the invention relates to any one of the aforementioned emulsions, wherein the first antioxidant or first preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the first antioxidant or first preservative comprises butylated hydroxytoluene.

In certain embodiments, the invention relates to any one of the aforementioned emulsions, wherein the first antioxidant or first preservative is present in an amount from about 0.01% to about 0.05% by weight of the emulsion. In certain embodiments, the first antioxidant or first preservative is present in an amount from about 0.02% to about 0.04% by weight of the emulsion. In certain embodiments, the first antioxidant or first preservative is present in an amount of about 0.01%, about 0.02%, about 0.03%, about 0.04%, or about 0.05% by weight of the emulsion.

In certain embodiments, the invention relates to any one of the aforementioned emulsions, wherein the first antioxidant or first preservative comprises butylated hydroxytoluene. In certain embodiments, the butylated hydroxytoluene is present in an amount from about 0.01% to about 0.05% by weight of the emulsion. In certain embodiments, the butylated hydroxytoluene is present in an amount from about 0.02% to about 0.04% by weight of the emulsion. In certain embodiments, the butylated hydroxytoluene is present in about 0.01%, about 0.02%, about 0.03%, about 0.04%, or about 0.05% by weight of the emulsion.

Exemplary Components of the Aqueous Phase

As outlined above, in certain embodiments, the invention relates to an emulsion comprising an aqueous phase, wherein the aqueous phase comprises water, a second moisturizer or second emollient, and a second antioxidant or second preservative. The components described below may be present in the aqueous phase of any one of the aforementioned emulsions.

In certain embodiments, the invention relates to any one of the aforementioned emulsions, wherein water is present in an amount about 27% to about 82% by weight of the emulsion. In certain embodiments, water is present in an amount from about 35% to about 75% by weight of the emulsion. In certain embodiments, water is present in an amount from about 40% to about 68% by weight of the emulsion. In certain embodiments, water is present in an amount of about 40%, about 42%, about 44%, about 46%, about 48%, about 50%, about 52%, about 54%, about 56%, about 58%, about 60%, about 62%, about 64%, about 66%, or about 68% by weight of the emulsion. In certain embodiments, the water is purified water.

In certain embodiments, the invention relates to any one of the aforementioned emulsions, wherein the second moisturizer or second emollient is selected from the group consisting of petrolatum, lactic acid, glycerol, propylene glycol, butylene glycol, sodium PCA, sodium hyaluronate, CARBOWAX PEG 200, CARBOWAX PEG 400, CARBOWAX PEG 800, cetyl palmitate, PPG-15 stearyl ether, lanolin alcohol, lanolin, lanolin derivatives, cholesterol, isostearyl neopentanoate, octyl stearate, mineral oil, isocetyl stearate, myristyl myristate, octyl dodecanol, 2-ethylhexyl palmitate, dimethicone, phenyl trimethicone, cyclomethicone, $C_{12}$-$C_{15}$ alkyl benzoates, dimethiconol, propylene glycol, *Theobroma grandiflorum* seed butter, ceramide 2, hydroxypropyl bispalmitamide MEA, hydroxypropyl bislauramide MEA, hydroxypropyl bisisostearamide MEA, 1,3-bis(N-2-(hydroxyethyl) stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, and dicaprylate/dicaprate and combinations/mixtures thereof.

In certain embodiments, the invention relates to any one of the aforementioned emulsions, wherein the second moisturizer or second emollient is selected from the group consisting of glycerol, urea, and combinations/mixtures thereof.

In certain embodiments, the invention relates to any one of the aforementioned emulsions, wherein the second moisturizer or second emollient is present in an amount from about 3% to about 9% by weight of the emulsion. In certain embodiments, the second moisturizer or second emollient is present in an amount from about 4% to about 8% by weight of the emulsion. In certain embodiments, the second moisturizer or second emollient is present in an amount of about 4%, about 5%, about 6%, about 7%, or about 8% by weight of the emulsion.

In certain embodiments, the invention relates to any one of the aforementioned emulsions, wherein the second moisturizer or second emollient comprises glycerol. In certain embodiments, the glycerol is present in an amount from about 2.5% to about 7.5% by weight of the emulsion. In certain embodiments, the glycerol is present in an amount from about 3% to about 7% by weight of the emulsion. In certain embodiments, the glycerol is present in about 3%, about 4%, about 5%, about 6%, or about 7% by weight of the emulsion.

In certain embodiments, the invention relates to any one of the aforementioned emulsions, wherein the second moisturizer or second emollient comprises urea. In certain embodiments, the urea is present in an amount from about 0.3% to about 0.9% by weight of the emulsion. In certain embodiments, the urea is present in an amount from about 0.4% to about 0.8% by weight of the emulsion. In certain embodiments, the urea is present in about 0.4%, about 0.5%, about 0.6%, about 0.7%, or about 0.8% by weight of the emulsion.

In certain embodiments, the invention relates to any one of the aforementioned emulsions, wherein the second antioxidant or second preservative is selected from the group consisting of imidazolidinyl urea, diazolidinyl urea, phenoxyethanol, sodium methyl paraben, methylparaben, ethylparaben, propylparaben, potassium sorbate, sodium benzoate, sorbic acid, benzoic acid, formaldehyde, citric acid, sodium citrate, chlorine dioxide, benzalkonium chloride, benzethonium chloride, cetrimide, dequalinium chloride, cetylpyridinium chloride, phenylmercuric nitrate, phenylmercuric acetate, thimerosal, piroctone olamine, *Vitis vinifera* seed oil, chlorobutanol, dichlorobenzyl alcohol, phenylethyl alcohol, benzyl alcohol, ascorbic acid, sodium bisulfite, butylated hydroxytoluene, butylated hydroxyanisole, α-tocopherol, tocopheryl acetate, sodium ascorbate/ascorbic acid, ascorbyl palmitate, propyl gallate, disodium EDTA, citric acid, and sodium citrate, and combinations/mixtures thereof.

In certain embodiments, the invention relates to any one of the aforementioned emulsions, wherein the second antioxidant or second preservative is selected from the group consisting of methylparaben, propylparaben, citric acid, sodium citrate, and combinations/mixtures thereof.

In certain embodiments, the invention relates to any one of the aforementioned emulsions, wherein the second antioxidant or second preservative is present in an amount from about 0.05% to about 1.5% by weight of the emulsion. In certain embodiments, the second antioxidant or second preservative is present in an amount from about 0.1% to about 1.4% by weight of the emulsion. In certain embodiments, the second antioxidant or second preservative is present in an amount of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, or about 1.4% by weight of the emulsion.

In certain embodiments, the invention relates to any one of the aforementioned emulsions, wherein the second antioxidant or second preservative comprises methylparaben. In certain embodiments, the methylparaben is present in an amount from about 0.1% to about 0.5% by weight of the emulsion. In certain embodiments, the methylparaben is present in an amount from about 0.2% to about 0.4% by weight of the emulsion. In certain embodiments, the methylparaben is present in about 0.2%, about 0.25%, about 0.3%, about 0.35%, or about 0.4% by weight of the emulsion.

In certain embodiments, the invention relates to any one of the aforementioned emulsions, wherein the second antioxidant or second preservative comprises propylparaben. In certain embodiments, the propylparaben is present in an amount from about 0.05% to about 0.2% by weight of the emulsion. In certain embodiments, the propylparaben is present in an amount from about 0.08% to about 0.12% by weight of the emulsion. In certain embodiments, the propylparaben is present in about 0.08%, about 0.09%, about 0.1%, about 0.11%, or about 0.12% by weight of the emulsion.

In certain embodiments, the invention relates to any one of the aforementioned emulsions, wherein the second antioxidant or second preservative comprises citric acid. In certain embodiments, the citric acid is present in an amount from about 0.2% to about 0.6% by weight of the emulsion. In certain embodiments, the citric acid is present in an amount from about 0.3% to about 0.5% by weight of the emulsion. In certain embodiments, the citric acid is present in about 0.3%, about 0.35%, about 0.4%, about 0.45%, or about 0.5% by weight of the emulsion.

In certain embodiments, the invention relates to any one of the aforementioned emulsions, wherein the second antioxidant or second preservative comprises sodium citrate. In certain embodiments, the sodium citrate is present in an amount from about 0.1% to about 0.5% by weight of the emulsion. In certain embodiments, the sodium citrate is present in an amount from about 0.15% to about 0.45% by weight of the emulsion. In certain embodiments, the sodium citrate is present in about 0.15%, about 0.2%, about 0.25%, about 0.3%, about 0.35%, about 0.4%, or about 0.45% by weight of the emulsion.

In certain embodiments, the invention relates to any one of the aforementioned emulsions, further comprising a buffer. In certain embodiments, the buffer is present in an amount from about 0.1% to about 1.5% by weight of the emulsion. In certain embodiments, the buffer is present in an amount from about 0.5% to about 1.0% by weight of the emulsion. In certain embodiments, the buffer is present about 0.5%, about 0.6%, about 0.7%, about 0.8%, about 0.9%, or about 1.0% by weight of the emulsion.

Exemplary Active Agents

As outlined above, in certain embodiments, the invention relates to an emulsion comprising an active agent. The components described below may be present in any one of the aforementioned emulsions.

In certain embodiments, the invention relates to any one of the aforementioned emulsions, wherein the active agent is present in an amount from about 0.002% to about 0.25% by weight of the emulsion. In certain embodiments, the invention relates to any one of the aforementioned emulsions, wherein the active agent is present in an amount from about 0.003% to about 0.20% by weight of the emulsion. In certain embodiments, the invention relates to any one of the aforementioned emulsions, wherein the active agent is present in about 0.003%, about 0.004%, about 0.005%, about 0.006%, about 0.007%, about 0.008%, about 0.009%, about 0.10%, about 0.11%, about 0.12%, about 0.13%, about 0.14%, about 0.15%, about 0.16%, about 0.17%, about 0.18%, about 0.19%, or about 0.20% by weight of the emulsion.

In certain embodiments, the invention relates to any one of the aforementioned emulsions, wherein the active agent is selected from the group consisting of corticosteroids, vitamin D analogues, retinoids, immunomodulators, antifungals, and combinations/mixtures thereof.

In certain embodiments, the invention relates to any one of the aforementioned emulsions, wherein the active agent is selected from the group consisting of hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone dipropionate, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and combinations/mixtures thereof.

In certain embodiments, the invention relates to any one of the aforementioned emulsions, wherein the active agent is selected from the group consisting of hydrocortisone butyrate, betamethasone dipropionate, and combinations/mixtures thereof.

In certain embodiments, the invention relates to any one of the aforementioned emulsions, wherein the active agent comprises hydrocortisone butyrate. In certain embodiments, the hydrocortisone butyrate is present in an amount from about 0.05% to about 0.25% by weight of the emulsion. In certain embodiments, the hydrocortisone butyrate is present in an amount from about 0.05% to about 0.20% by weight of the emulsion. In certain embodiments, the hydrocortisone butyrate is present in about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, or about 0.20% by weight of the emulsion.

In certain embodiments, the invention relates to any one of the aforementioned emulsions, wherein the active agent comprises betamethasone dipropionate. In certain embodiments, the betamethasone dipropionate is present in an amount from about 0.02% to about 0.08% by weight of the emulsion. In certain embodiments, the betamethasone dipropionate is present in an amount from about 0.03% to about 0.07% by weight of the emulsion. In certain embodiments, the betamethasone dipropionate is present in about 0.03%, about 0.04%, about 0.05%, about 0.06%, or about 0.07% by weight of the emulsion.

In certain embodiments, the invention relates to any one of the aforementioned emulsions, wherein the active agent is selected from the group consisting of vitamin A, vitamin D, vitamin E, vitamin K, vitamin D analogue calcipotriene, vitamin D analogue calcipotriol, and combinations/mixtures thereof.

In certain embodiments, the invention relates to any one of the aforementioned emulsions, wherein the active agent comprises calcipotriene. In certain embodiments, the calcipotriene is present in an amount from about 0.002% to about 0.008% by weight of the emulsion. In certain embodiments, the calcipotriene is present in an amount from about 0.003% to about 0.007% by weight of the emulsion. In certain embodiments, the calcipotriene is present in about 0.003%, about 0.004%, about 0.005%, about 0.006%, or about 0.007% by weight of the emulsion.

In certain embodiments, the invention relates to any one of the aforementioned emulsions, wherein the active agent is selected from the group consisting of retinoids such as retinoic acid (e.g., tretinoin) and its derivatives (e.g., cis and trans, esters), and combinations/mixtures thereof.

In certain embodiments, the invention relates to any one of the aforementioned emulsions, wherein the active agent comprises tretinoin. In certain embodiments, the tretinoin is present in an amount from about 0.01% to about 0.03% by weight of the emulsion. In certain embodiments, the tretinoin is present in an amount from about 0.015% to about 0.025% by weight of the emulsion. In certain embodiments, the tretinoin is present in about 0.015%, about 0.016%, about 0.017%, about 0.018%, about 0.019%, about 0.020%, about 0.021%, about 0.022%, about 0.023%, about 0.024%, or about 0.025% by weight of the emulsion.

In certain embodiments, the invention relates to any one of the aforementioned emulsions, wherein the active agent is selected from the group consisting of tacrolimus, pimecrolimus, tetrachlorodecaoxide, deoxycholic acid, beta-glucan, and combinations/mixtures thereof.

In certain embodiments, the invention relates to any one of the aforementioned emulsions, wherein the active agent is selected from the group consisting of beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

Exemplary Compositions of the Invention

In certain embodiments, the invention relates to a composition, comprising:
  any one of the aforementioned emulsions;
  a propellant; and
  a purge gas.

In certain embodiments, the invention relates to a composition, consisting essentially of:
  any one of the aforementioned emulsions;
  a propellant; and
  a purge gas.

In certain embodiments, the invention relates to a composition, consisting of:
  any one of the aforementioned emulsions;
  a propellant; and
  a purge gas.

Exemplary Propellants

As outlined above, in certain embodiments, the invention relates to a composition comprising an emulsion, a propellant, and a purge gas. The propellants described below may be present in any one of the aforementioned compositions.

In certain embodiments, the invention relates to any one of the aforementioned compositions, wherein the propellant is selected from the group consisting of 1,1,1,2-tetrafluoroethane, 1,1,1,2,3,3,3-heptafluoropropane, and combinations/mixtures thereof.

In certain embodiments, the invention relates to any one of the aforementioned compositions, wherein the propellant is present in an amount from about 3% to about 20% by weight of the composition. In certain embodiments, the invention relates to any one of the aforementioned compositions, wherein the propellant is present in an amount from about 5% to about 18% by weight of the composition. In certain embodiments, the invention relates to any one of the aforementioned compositions, wherein the propellant is about 5%, about 6%, about 7%, about 8%, about 9%, about 10%, about 11%, about 12%, about 13%, about 14%, about 15%, about 16%, about 17%, or about 18% by weight of the composition.

Exemplary Purge Gases

As outlined above, in certain embodiments, the invention relates to a composition comprising an emulsion, a propellant, and a purge gas. The purge gases described below may be present in any one of the aforementioned compositions.

In certain embodiments, the invention relates to any one of the aforementioned compositions, wherein the purge gas is selected from the group consisting of nitrogen and argon. In certain embodiments, the invention relates to any one of the aforementioned compositions, wherein the purge gas is argon.

In certain embodiments, the invention relates to any one of the aforementioned compositions, wherein the purge gas is present in an amount from about 0.4% to about 6% by weight of the composition. In certain embodiments, the invention relates to any one of the aforementioned compositions, wherein the purge gas is present in an amount from about 0.8% to about 5% by weight of the composition. In certain embodiments, the invention relates to any one of the aforementioned compositions, wherein the purge gas is about 0.8%, about 1%, about 1.2%, about 1.4%, about 1.6%, about 1.8%, about 2%, about 2.2%, about 2.5%, about 2.6%, about 2.8%, about 3%, about 3.2%, about 3.4%, about 3.6%, about 3.8%, about 4%, about 4.2%, about 4.4%, about 4.6%, about 4.8% or about 5% by weight of the composition.

Exemplary Properties of Emulsions and Compositions of the Invention

In certain embodiments, the invention relates to any one of the aforementioned emulsions or compositions that, upon application to the skin of an affected subject, is non-irritating.

In certain embodiments, the invention relates to any one of the aforementioned emulsions or compositions that, upon application to the skin of an affected subject, is well-tolerated.

In certain embodiments, the invention relates to any one of the aforementioned emulsions or compositions that, upon application to the skin of an affected subject, reduces inflammation.

In certain embodiments, the invention relates to any one of the aforementioned emulsions or compositions that, upon application to the skin of an affected subject, is non-cytotoxic.

In certain embodiments, the invention relates to any one of the aforementioned emulsions or compositions that, upon application to the skin of an affected subject, is weakly sensitizing. In certain embodiments, the invention relates to any one of the aforementioned emulsions or compositions that, upon application to the skin of an affected subject, is non-sensitizing.

In certain embodiments, the invention relates to any one of the aforementioned emulsions or compositions that, upon application to the skin of an affected subject, does not produce edema or erythema.

In certain embodiments, the invention relates to any one of the aforementioned emulsions or compositions that, upon application to the skin of an affected subject, moisturizes the skin.

In certain embodiments, the invention relates to any one of the aforementioned emulsions or compositions that, upon application to the skin of an affected subject, increases hydration of the skin.

In certain embodiments, the invention relates to any one of the aforementioned emulsions or compositions that, upon application to the skin of an affected subject, reduces transepidermal water loss.

In certain embodiments, the invention relates to any one of the aforementioned emulsions, wherein the emulsion has a viscosity of from about 75,000 cps to about 450,000 cps. In certain embodiments, the invention relates to any one of the aforementioned emulsions, wherein the emulsion has a viscosity of from about 100,000 cps to about 350,000 cps. In certain embodiments, the invention relates to any one of the aforementioned emulsions, wherein the emulsion has a viscosity of from about 150,000 cps to about 250,000 cps. In certain embodiments, the invention relates to any one of the aforementioned emulsions, wherein the emulsion has a viscosity of about 100,000 cps, about 125,000 cps, about 150,000 cps, about 175,000 cps, about 200,000 cps, about 225,000 cps, about 250,000 cps, about 275,000 cps, about 300,000 cps, about 325,000 cps, or about 350,000 cps.

In certain embodiments, the invention relates to any one of the aforementioned compositions that, upon expulsion from an aerosol container, forms a foam. In certain embodiments, the foam is temperature-stable. In certain embodiments, the foam is time-stable. In certain embodiments, the density of the foam is from about 0.05 to about 0.5 $g/cm^3$. In certain embodiments, the invention relates to any one of the aforementioned compositions that is easily shaken in an aerosol container. In certain embodiments, the invention relates to any one of the aforementioned compositions that is easily dispensed from an aerosol container.

Exemplary Emulsions and Compositions of the Invention for Particular Uses

In certain embodiments, the invention relates to any one of the aforementioned emulsions or compositions for use in the treatment of an inflammatory skin disorder.

In certain embodiments, the invention relates to any one of the aforementioned emulsions or compositions for use in the treatment of psoriasis, atopic dermatitis, contact dermatitis, xerotic eczema, seborrheic dermatitis, discoid eczema, venous eczema, acne, rosacea, poison ivy, hives, or occupational dermatitis.

In certain embodiments, the invention relates to any one of the aforementioned emulsions or compositions for use in the treatment of psoriasis or atopic dermatitis.

In certain embodiments, the invention relates to any one of the aforementioned emulsions or compositions for use in the treatment of an inflammatory skin disorder, wherein the emulsion or composition is formulated for topical application once daily or twice daily.

Exemplary Methods of Use

In certain embodiments, the invention relates to a method of treating an inflammatory skin disorder, comprising the step of applying to an affected area of a subject in need thereof a therapeutically-effective amount of any one of the aforementioned emulsions or compositions.

In certain embodiments, the invention relates to any one of the aforementioned methods, wherein the inflammatory skin disorder is psoriasis, atopic dermatitis, contact dermatitis, xerotic eczema, seborrheic dermatitis, discoid eczema, venous eczema, acne, rosacea, poison ivy, hives, or occupational dermatitis.

In certain embodiments, the invention relates to any one of the aforementioned methods, wherein the inflammatory skin disorder is psoriasis or atopic dermatitis.

In one embodiment, the present invention relates to any one of the above-mentioned methods, wherein the condition is atopic dermatitis. In one embodiment, the present invention relates to any one of the above-mentioned methods, wherein the condition is atopic dermatitis with more than about 10% body surface area (BSA) involvement. In one embodiment, the present invention relates to any one of the above-mentioned methods, wherein the condition is atopic dermatitis with up to about 80% body surface area (BSA) involvement.

In one embodiment, the present invention relates to any one of the above-mentioned methods, wherein the subject is human.

In one embodiment, the present invention relates to the above-mentioned method, wherein the affected area of the subject is the face, earlobes, neck, scalp, genitals, eyelids, palms, fingers, feet, exural surfaces of joints, or extensor aspects of joints. In one embodiment, the present invention relates to the above-mentioned method, wherein the affected area of the subject is the face. In one embodiment, the present invention relates to the above-mentioned method, wherein the affected area of the subject is the exural (inner) surfaces of elbows or knees. In one embodiment, the present invention relates to the above-mentioned method, wherein the affected area of the subject is the extensor aspects of wrists, elbows, ankles, or knees In one embodiment, the present invention relates to any one of the above-mentioned methods, wherein the composition is applied once daily.

In one embodiment, the present invention relates to any one of the above-mentioned methods, wherein the composition is applied twice daily.

EXEMPLIFICATION

The invention now being generally described, it will be more readily understood by reference to the following examples which are included merely for purposes of illustration of certain aspects and embodiments of the present invention, and are not intended to limit the invention.

Example 1

Compositions and Method of Manufacture

An example product concentrate (NB249-99) can be manufactured by the procedure outlined below:
Part A: Oil Phase Preparation
1. Charge Ceteth-20 (I) light mineral oil, white petrolatum, dimethicone, safflower oil, butylated hydroxytoluene and cetostearyl alcohol into a stainless steel tank and heat until fully melted.
Part B: Aqueous Phase Preparation
1. Charge Purified Water (I) and Glycerin into a stainless steel tank and heat to 75-80° C.
2. Charge and dissolve citric acid (I) and sodium citrate (I) as well as urea, methyl paraben and propyl paraben while mixing.
3. Continue mixing until a clear solution is obtained while maintaining a temperature of 65-95° C.
Part C: Drug Phase Preparation
1. Charge a Stainless Steel tank with Purified Water (II), citric acid (II), sodium citrate (II) and Ceteth-20 (II).
2. Mix slowly at room temperature to dissolve.
3. Add hydrocortisone butyrate and mix until fully wetted and dispersed.
Part D: Drug Product Concentrate Formation
1. Add Part A to Part B while high-shear mixing at 65-95° C.
2. Cool the emulsion with an outside cold-water jacket to below 50° C. while high-shear mixing.
3. Discontinue high-shear mixing. Start low-shear mixing and continue cooling with cold-water jacket to form the vehicle emulsion.
4. When the temperature of the vehicle emulsion is below 37° C., add Part C and continue mixing until uniform.
5. Cool to room temperature. Adjust to final volume with DI water. Mix until uniform.

Following manufacturing of the drug product and vehicle concentrate, the finished drug product and drug product vehicle is produced as outlined below:
1. Aerosol cans are cleaned with compressed air and vacuum.
2. Product concentrate is filled into cans.
3. Valves are placed onto the cans.
4. Cans are crimped and hydrofluorcarbon propellant is charged.
5. The aerosol can valve and dip-tube is purged with argon gas.

Propellant concentrations range from 8-15% by weight of packaged product, argon concentrations range from 0.8-4.0% by weight of packaged product Example 2

Active Ingredients

In addition to the corticosteroid hydrocortisone butyrate, other corticosteroid active ingredients can be incorporated into the compositions of the invention. Other classes of active ingredients may also be incorporated into the compositions of the invention including vitamin-D analogs, retinoids, immunomodulators, antifungals and combinations of these active ingredients with each other or with corticosteroids. The example emulsions depicted in FIG. 4 were prepared as described in Example 1.

Example 3

Emulsion Viscosities

Vehicle viscosity influences the ability of the emulsion to hold an active pharmaceutical ingredient (API) in suspension, the physical stability of the emulsion, and the density, delivery rate, and delivered amount of dispensed foam. Low formulation viscosities allow the API to settle out of suspension, leading to issues of content uniformity and allow the emulsion droplets to segregate in the formulation leading to phase separation. Viscosities above approximately 280,000 cP prevent the composition from moving in the can causing propellant tunneling which leads to inconsistent delivery rate and delivered amount for the dispensed foam. High viscosity also results in a dispensed foam with poor tactile properties.

The relationship between oil phase composition and viscosity was examined. In topical formulations, the co-surfactant cetostearyl alcohol builds viscosity and foam density. Oil phase concentration and components also influence drug product viscosity. The viscosities of emulsions from Example 1 as well as additional emulsions were measured under low shear conditions to determine the ability of the emulsions to flow during container actuation (FIG. 5 and FIG. 6).

Variations in the percentages of liquid lipids and cetostearyl alcohol had large effects on viscosity. As the percentage of cetostearyl alcohol increased, the viscosity rapidly increased; increases in the concentration of liquid oil phase had much less of an effect on viscosity.

Example 4

Product Densities

When dispensed from an aerosol can, the compositions of the invention form time- and temperature-stable low-density foams (FIG. 7). The densities of dispensed foam and non-foam compositions were measured as follows.

Product was dispensed into a conical receptacle of known weight and volume. The product was dispensed into the receptacle so that there are no voids. Excess material was removed from the top of the receptacle with a flat-bladed spatula. The mass of the test article and receptacle was determined with the test article density calculated using the formula:

$$\text{Density} = (\text{MASS}_T - \text{MASS}_R)/\text{VOLUME}_R$$

Where:
$\text{MASS}_T$ = total mass of test article and receptacle
$\text{MASS}_R$ = mass of receptacle
$\text{VOLUME}_R$ = volume of receptacle

Example 5

Formulation Stability in the Presence of Hydrofluorocarbon Propellants

The in-packaging physical stability of aerosol foam concentrates has a significant effect on their efficacy and consumer acceptability. Oil-in-water emulsion formulations such as the formulations of the invention are traditionally thermodynamically unstable and therefore will separate into two or more phases over time. The time required for this physical instability to manifest is dependent on temperature; higher temperatures tend to accelerate the separation of phases. While the oil and water phase compositions are well-known to affect formulation stability, variations in propellant composition within a propellant class are also considered to be a factor.

Fourteen different formulation variants were prepared and packaged in the presence of either HFA-134a or 50/50 blend of HFA-134a and HFA-227 and stored at 40° C. FIG. 8 summarizes the relative ratios of emollient oil, surfactant, and co-surfactant, the aerosol propellant, and the number of days stable for each of the packaged formulations.

Figure 10:
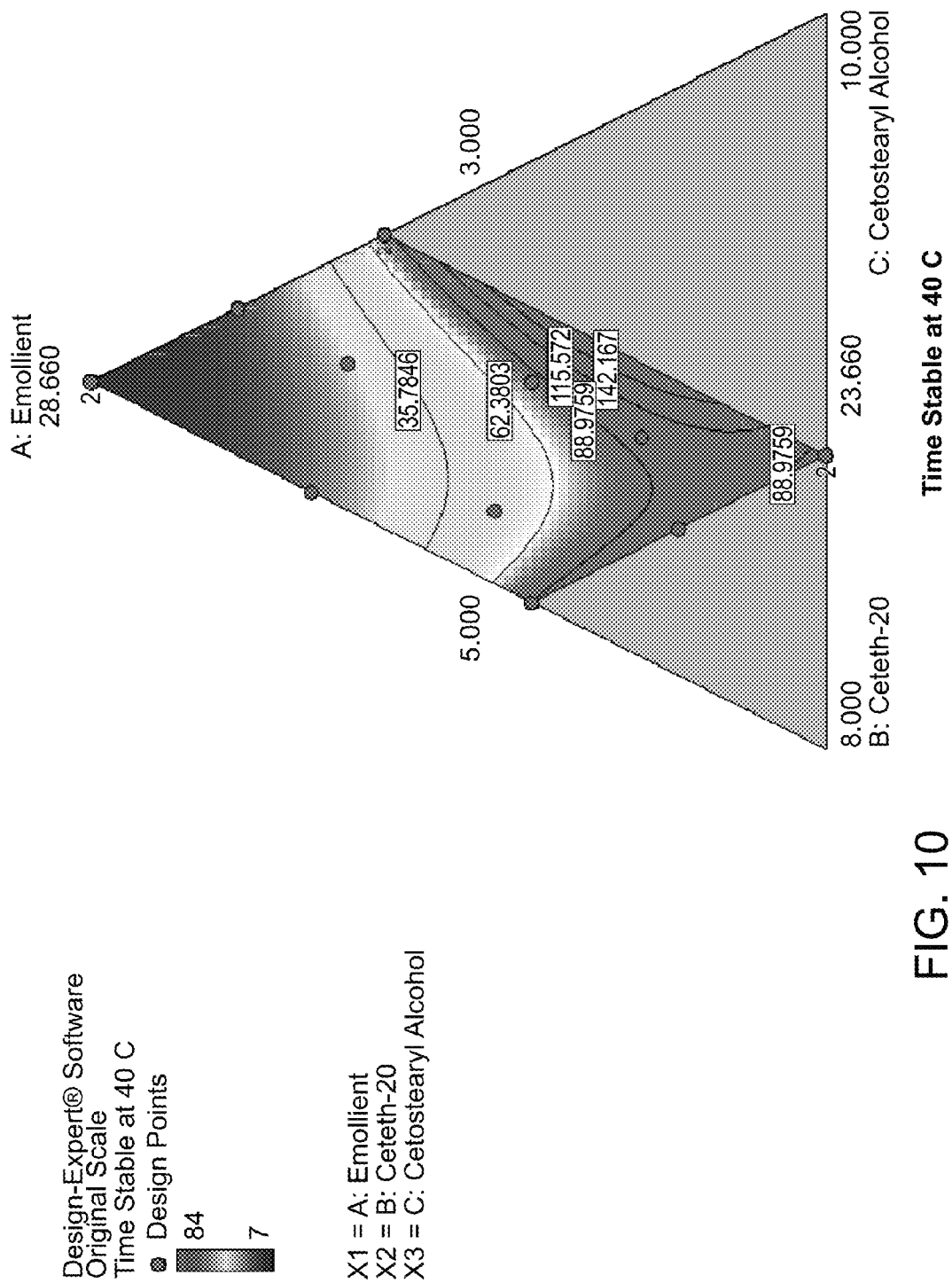
FIG. 10 is a schematic representation of the dependence of composition physical stability (days stable, ranging from 7 (black to 84 (gray), with light gray in between) on the ratios of emollient oil, Ceteth-20, and cetostearyl alcohol in the presence of 1,1,1,2-tetrafluoroethane and 1,1,1,2,3,3,3-heptafluoropropane. It is interesting to note that the stability of these formulations is dictated by the concentration of emollient in the formulation (vertical axis).

As can be seen from FIG. 8, the formulations exhibited significantly different physical stabilities in the presence of the two aerosol propellants. This is further illustrated in FIG. 9 and FIG. 10. The stability of formulations in the presence of HFA-134a is relatively insensitive to the concentration of emollient oil and is primarily driven by the surfactant/co-surfactant ratio. In contrast, the stability of formulations in the presence of the HFA-134a/HFa-227 blend is insensitive to the surfactant/co-surfactant ratio and is dictated by the concentration of emollient oil.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating an inflammatory skin disorder, comprising the step of applying to an affected area of a subject in need thereof a therapeutically-effective amount of a composition comprising:
    an emulsion, wherein the emulsion comprises
        Ceteth-20, from about 1% to about 5% by weight of the emulsion;
        cetostearyl alcohol, from about 3% to about 9% by weight of the emulsion;
        mineral oil, from about 1% to about 18% by weight of the emulsion;
        petrolatum, from about 3% to about 11% by weight of the emulsion;
        dimethicone, from about 0.5% to about 2.0% by weight of the emulsion;
        butylated hydroxytoluene, from about 0.01% to about 0.05% by weight of the emulsion;
        water, from about 27% to about 82% by weight of the emulsion;
        glycerin, from about 2.5% to about 7.5% by weight of the emulsion;
        urea, from about 0.3% to about 0.9% by weight of the emulsion;
        citric acid, from about 0.2% to about 0.6% by weight of the emulsion;
        sodium citrate, from about 0.1% to about 0.5% by weight of the emulsion;
        methylparaben, from about 0.1% to about 0.5% by weight of the emulsion;
        propylparaben, from about 0.05% to about 0.20% by weight of the emulsion; and
        an active agent, from about 0.002% to about 0.20% by weight of the emulsion;
    a propellant; and
    a purge gas.

2. The method of claim 1, wherein the inflammatory skin disorder is selected from the group consisting of psoriasis, atopic dermatitis, contact dermatitis, xerotic eczema, seborrheic dermatitis, discoid eczema, venous eczema, acne, rosacea, poison ivy, hives, and occupational dermatitis.

3. The method of claim 2, wherein the subject is human.

4. The method of claim 3, wherein the affected area of the subject is the face, earlobes, neck, scalp, genitals, eyelids, palms, fingers, feet, exural surfaces of joints, or extensor aspects of joints.

5. The method of claim 4, wherein the composition is applied once daily or twice daily.

6. The method of claim 1, wherein the active agent is selected from the group consisting of corticosteroids, vitamin D analogues, retinoids, immunomodulators, antifungals, and combinations/mixtures thereof.

7. The method of claim 1, wherein the active agent is selected from the group consisting of hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone dipropionate, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and combinations/mixtures thereof.

8. The method of claim 1, wherein the active agent is selected from the group consisting of hydrocortisone butyrate, betamethasone dipropionate, and combinations/mixtures thereof.

9. The method of claim 1, wherein the active agent is selected from the group consisting of vitamin A, vitamin D, vitamin E, vitamin K, vitamin D analogue calcipotriene, vitamin D analogue calcipotriol, and combinations/mixtures thereof.

10. The method of claim 1, wherein the active agent is selected from the group consisting of retinoids, retinoic acid, tretinoin, and combinations/mixtures thereof.

11. The method of claim 1, wherein
the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 54.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion; and
the emulsion further comprises safflower oil, in about 6.75% by weight of the emulsion.

12. The method of claim 1, wherein
the emulsion comprises
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 55.46% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
hydrocortisone butyrate, in about 0.10% by weight of the emulsion; and
the emulsion further comprises
safflower oil, in about 6.75% by weight of the emulsion;
oleic acid, in about 0.50% by weight of the emulsion; and
stearic acid, in about 0.50% by weight of the emulsion.

13. The method of claim 1, wherein
the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion; and
the emulsion further comprises safflower oil, in about 6.75% by weight of the emulsion.

14. The method of claim 1, wherein
the emulsion comprises:
Ceteth-20, in about 3.00% by weight of the emulsion;
cetostearyl alcohol, in about 6.00% by weight of the emulsion;
mineral oil, in about 2.38% by weight of the emulsion;
petrolatum, in about 6.85% by weight of the emulsion;
dimethicone, in about 1.00% by weight of the emulsion;
butylated hydroxytoluene, in about 0.03% by weight of the emulsion;
water, in about 56.51% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
betamethasone dipropionate, in about 0.05% by weight of the emulsion; and
the emulsion further comprises
oleic acid, in about 7.40% by weight of the emulsion; and
oleyl alcohol, in about 10.00% by weight of the emulsion.

15. The method of claim 1, wherein
the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;

butylated hydroxytoluene, in about 0.03% by weight of the emulsion;
water, in about 56.54% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
tretinoin, in about 0.02% by weight of the emulsion; and
the emulsion further comprises safflower oil, in about 6.75% by weight of the emulsion.

16. The method of claim 1, wherein the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 56.555% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion; and
calcipotriene, in about 0.005% by weight of the emulsion; and
the emulsion further comprises safflower oil, in about 6.75% by weight of the emulsion.

17. The method of claim 1, wherein the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 56.505% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion;
betamethasone dipropionate, in about 0.05% by weight of the emulsion; and
calcipotriene, in about 0.005% by weight of the emulsion; and
the emulsion further comprises safflower oil, in about 6.75% by weight of the emulsion.

18. The method of claim 1, wherein the emulsion comprises:
Ceteth-20, in about 3.00% by weight of the emulsion;
cetostearyl alcohol, in about 6.00% by weight of the emulsion;
mineral oil, in about 12.38% by weight of the emulsion;
petrolatum, in about 7.50% by weight of the emulsion;
dimethicone, in about 1.00% by weight of the emulsion;
butylated hydroxytoluene, in about 0.03% by weight of the emulsion;
water, in about 56.49% by weight of the emulsion;
glycerin, in about 5.00% by weight of the emulsion;
urea, in about 0.64% by weight of the emulsion;
citric acid, in about 0.42% by weight of the emulsion;
sodium citrate, in about 0.32% by weight of the emulsion;
methylparaben, in about 0.30% by weight of the emulsion;
propylparaben, in about 0.10% by weight of the emulsion;
betamethasone dipropionate, in about 0.05% by weight of the emulsion; and
tretinoin, in about 0.02% by weight of the emulsion; and
the emulsion further comprises safflower oil, in about 6.75% by weight of the emulsion.

19. The method of claim 1, wherein the propellant is selected from the group consisting of 1,1,1,2-tetrafluoroethane, 1,1,1,2,3,3,3-heptafluoropropane, and combinations/mixtures thereof.

20. The method of claim 1, wherein the purge gas is selected from the group consisting of nitrogen and argon.

* * * * *